(12) United States Patent
Pickover et al.

(10) Patent No.: US 10,930,377 B2
(45) Date of Patent: Feb. 23, 2021

(54) DENTAL HEALTH TRACKING VIA BLOCKCHAIN

(71) Applicant: INTERNATIONAL BUSINESS MACHINES CORPORATION, Armonk, NY (US)

(72) Inventors: Clifford A. Pickover, Yorktown Heights, NY (US); Komminist Weldemariam, Nairobi (KE)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 609 days.

(21) Appl. No.: 15/689,536

(22) Filed: Aug. 29, 2017

(65) Prior Publication Data

US 2019/0065685 A1 Feb. 28, 2019

(51) Int. Cl.
| | |
|---|---|
| *G16H 10/60* | (2018.01) |
| *G06F 21/60* | (2013.01) |
| *G06F 21/62* | (2013.01) |
| *G06F 21/64* | (2013.01) |
| *H04L 9/32* | (2006.01) |

(52) U.S. Cl.
CPC .......... *G16H 10/60* (2018.01); *G06F 21/602* (2013.01); *G06F 21/6245* (2013.01); *G06F 21/64* (2013.01); *H04L 9/3239* (2013.01); *H04L 9/3297* (2013.01); *H04L 2209/38* (2013.01); *H04L 2209/56* (2013.01)

(58) Field of Classification Search
CPC ................................................ G06Q 50/22–24
See application file for complete search history.

(56) References Cited

U.S. PATENT DOCUMENTS

| | | | |
|---|---|---|---|
| 9,998,286 B1* | 6/2018 | Ramathal | G16H 40/63 |
| 2005/0221401 A1* | 10/2005 | Nomura | A61B 10/0051 435/7.32 |
| 2011/0182406 A1* | 7/2011 | Nelson | A61B 6/4216 378/62 |
| 2013/0060144 A1* | 3/2013 | Culjat | A61B 8/14 600/459 |
| 2017/0173262 A1* | 6/2017 | Veltz | A61M 5/1723 |
| 2018/0028063 A1* | 2/2018 | Elbaz | A61B 5/0062 |
| 2018/0189449 A1* | 7/2018 | Karumba | G16H 40/20 |
| 2018/0264347 A1* | 9/2018 | Tran | G16H 20/30 |

\* cited by examiner

*Primary Examiner* — Robert A Sorey
(74) *Attorney, Agent, or Firm* — F. Chau & Associates, LLC

(57) ABSTRACT

A method for managing dental records using a blockchain includes receiving, from a dental device, one or more signals associated with a dental activity being performed by the dental device, detecting dental feature indictors with associated confidence levels by analyzing the dental signals, aggregating the dental feature indictors to compute a multi-dimensional feature vector, and determining whether to append the multi-dimensional feature vector to the blockchain.

10 Claims, 9 Drawing Sheets

|          | Tx Date    | T... | Code | Tooth | Surf... | Description |
|----------|------------|------|------|-------|---------|-------------|
| Complete | 08/21/2002 | R    | 4341 | UR    |         | Perio scaling-root plane/quad |
|          | 08/28/2003 | R    | 2335 | 8     | MIL     | Resin-four surf or inc angle, anterior |
| Existing | 08/28/2003 | R    | 2335 | 9     | MIL     | Resin-four surf or inc angle, anterior |
|          | 07/22/2004 | R    | 4910 |       |         | Periodontal maintenance |
|          | 08/23/2004 | R    | 3330 | 3     |         | Root canal-molar |
| T Plan   | 10/05/2005 | R    | 2750 | 4     |         | Crown-porcelain/high noble metal |
|          | 10/05/2004 | R    | 2750 | 5     |         | Crown-porcelain/high noble metal |
|          | 03/31/2006 | R    | 2750 | 12    |         | Crown-porcelain |
FIG. 1C
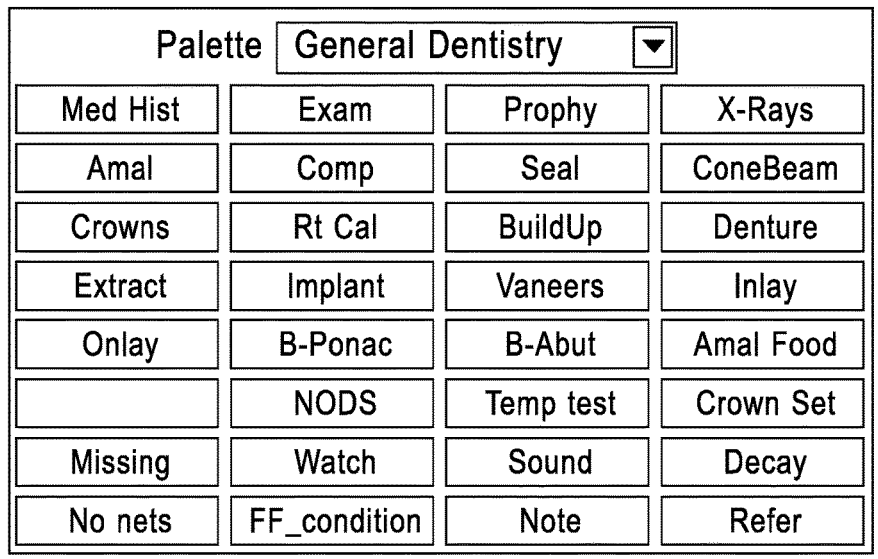
FIG. 1D
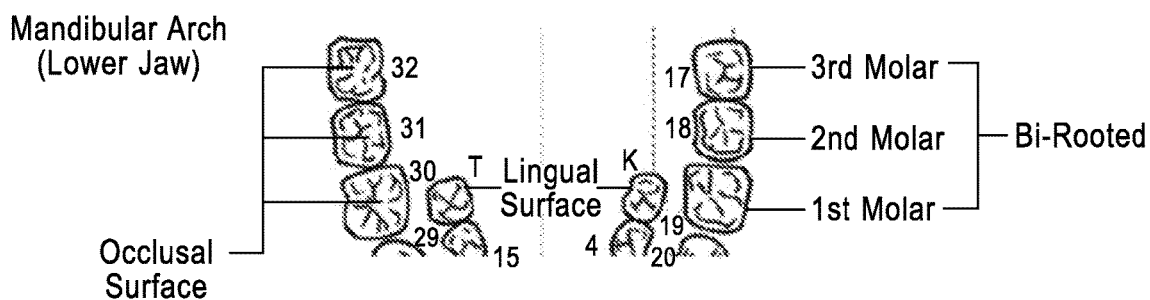
FIG. 1E

DENTAL HEALTH TRACKING VIA BLOCKCHAIN

BACKGROUND

Technical Field

Embodiments of the disclosure are directed to using a blockchain to maintain dental records.

Discussion of the Related Art

A blockchain is a distributed database that maintains a continuously-growing list of data records that are resistant to tampering and revision. A blockchain includes data structure blocks which can hold data and programs in recent implementations, in which each block contains batches of individual transactions and the results of any blockchain executables. Each block contains a timestamp and a link to a previous block.

Dentistry is especially suitable for blockchain applications. It is digital, in the sense that each tooth may have a record through time; it is a field that is sometimes subject to medical misinterpretation or over-treatment; and it has implications even beyond the medicine and health, having implications for crime cases, missing persons, forensics, and person identification. In addition, dentistry is special in that there are repeated transactions related to the same object through time, more so than other typical medical applications. Dental records include documents related to the history of a present illness, clinical examination, diagnosis, treatment done, and prognosis. A thorough knowledge of dental records is essential for a practicing dentist, as it not only has a forensic application, but also a legal implication with respect to insurance and consumerism. For example, not only can the age of a human specimen be narrowed by evaluating the patterns of tooth eruption and tooth wear, recent studies provide evidence that cementum, the mineralized tissue that lines the surface of tooth roots, exhibits annual patterns of deposition.

Going to the dentist involves a certain level of trust, in that most people lack the expertise to evaluate a diagnosis. However, the health care business lacks a single truth as a means for trust. For example, the U.S. National Health Care Anti-Fraud Association estimates that financial losses due to dentalcare fraud are in the tens of billions of dollars. Dental fraud takes a large part due to inflated and imaginary insurance claims, submission of multiple claims, questionable filling extractions, dental bullying, and other unnecessary procedures Dental records can "evolve" independently of a primary central database, and alteration of records is possible for financial gain. Records can be modified and altered by different stakeholders in different subjects as a patient may be admitted in more than one dentistry. Dental records management is a suitable application for a blockchain-enabled records management system that can store, track and manage transactions related to dental events, primarily for improved dental health and secondarily for applications such as dispute resolution, fraud detection and forensics, such as after a person has died or has gone missing. For example, with a blockchain, the alteration of dental records can be verified against a particularly useful instance of a patient's dental record. A mouth/tooth block may also contain information on DNA and dentin pulp complexes, which are useful for forensic application to determine a possible causes of death.

SUMMARY

Exemplary embodiments of the disclosure use blockchain technology to securely track and maintain a record of tooth history and events for a person. Tooth transactions associated with a stakeholder are compiled into a chain of mouth/tooth transaction blocks. The chain can be considered a chronicle of person's dental/tooth path through time. When a transaction occurs, one or more corresponding dental/tooth parameters, such as treatment, cavity detection, adjacent gum disease, cleaning information, filling material used, x-ray information, etc., are sent to one or more validation computing nodes/peers. The computing nodes/peers establish a validity of the transaction and generate a new block. Once the new block has been calculated it can be appended to the stakeholder's tooth historic blockchain. Embodiments can focus a block on an organ, such as a mouth/tooth and its possible impact on forensics, rather than on traditional medical health records of a person.

According to an embodiment of the disclosure, there is provided a method for managing dental records using a blockchain, including receiving, from a dental device, one or more signals associated with a dental activity being performed by the dental device, detecting dental feature indictors with associated confidence levels by analyzing the dental signals, aggregating the dental feature indictors to compute a multi-dimensional feature vector, and determining whether to append the multi-dimensional feature vector to the blockchain.

According to a further embodiment of the disclosure, determining whether to append the multi-dimensional feature vector to the blockchain includes creating a transaction for the multi-dimensional feature vector, sending the transaction to validating peers on the blockchain network for validation, receiving validation outputs by a consensus algorithm, where the validation outputs are generated by chaincodes executed by the validation peers using validity requirements with respect to the dental events associated with the transaction, and writing a new block for the transaction to the blockchain, when the consensus algorithm validates the transaction.

According to a further embodiment of the disclosure, the blockchain includes a record of a patient's dental related features and events through the life of the patient, or for a predetermined period of time, where the dental related features and events include information on one or more of cavities, gum disease, dry sockets, impacted teeth, malocclusion, toothwear, sinusitis, neuralgia, cracked teeth, fractured teeth, abrasion, missing teeth, erosion, attrition, bruxism, fracture, worn fillings, worn tooth enamel, and exposed roots; sensitivity to heat, cold, and sweets; filling materials, X-rays treatments, fluoride treatments, pulpotomies, pulpectomies, apicoectomies, veneers, bridges, implants, fiberotomies, implants, crowns, root canals; observations regarding color and discoloration; diet and pain level; interactions with dental technology; and interactions with a dental care professionals or automated dental systems.

According to a further embodiment of the disclosure, the dental device includes a home signal-enabled toothbrush, a dental office tooth cleaner, a signal-enabled dental office tooth probe, an X-ray machine, a dental office camera, and the one or more events associated with a dental activity include X-ray, treatments, teeth cleaning, teeth probing, and teeth and gum observations.

According to a further embodiment of the disclosure, the method includes automatically changing a rate of generating transactions related to a dental record based on a risk assessment or forecast.

According to a further embodiment of the disclosure, where the method includes changing a type of information added written to the blockchain based on a context of a patient.

According to another embodiment of the disclosure, there is provided an apparatus for managing dental records using a blockchain, including a distributed repository to securely store and maintain dental records, a risk assessor that analyzes event streams and historical block identifiers to characterize a patient's dental condition and context, and determine a risk to the patient's teeth, a content analyzer that analyzes documents, a patient's age, overall health, and number of remaining real teeth to determine what content to append to the distributed repository, and a transaction composer that uses the event streams and analysis results and prepares content to be appended to the distributed repository and appends the content to the distributed repository.

According to a further embodiment of the disclosure, the distributed repository is a blockchain.

According to a further embodiment of the disclosure, the apparatus includes a plurality of instruments and sensors at various locations that monitor and collect various events and data from a plurality of data sources.

According to a further embodiment of the disclosure, the plurality of instruments and sensors includes electronic toothbrush sensors, visual analytics, and dental instruments.

According to a further embodiment of the disclosure, the apparatus includes a validation device that obtains a historical block identifier from a historical dental blockchain representative of historical activities a patient conducted with respect to a tooth; receives one or more validity requirements with respect to the patient's tooth related activities; obtains a validation token indicative of a validity of the patient's actions based on a set of tokens comprising one or more inputs; and executes a smart contract/chaincode for a transaction against the validity requirements as a function of the validation token, the historical tooth's block identifier, and the set of tooth tokens.

According to another embodiment of the disclosure, there is provided a non-transitory program storage device readable by a computer, tangibly embodying a program of instructions executed by the computer to perform the method steps for managing dental records using a blockchain.

BRIEF DESCRIPTION OF THE DRAWINGS

FIG. 1C illustrates dental transaction records added to a blockchain block, according to an embodiment of the disclosure.

FIG. 1D illustrates additional exemplary, non-limiting buttons for adding blocks to the blockchain, according to an embodiment of the disclosure.

FIG. 1E depicts a tooth numbering system, according to an embodiment of the disclosure.

DETAILED DESCRIPTION OF EXEMPLARY EMBODIMENTS

Figure 1A:
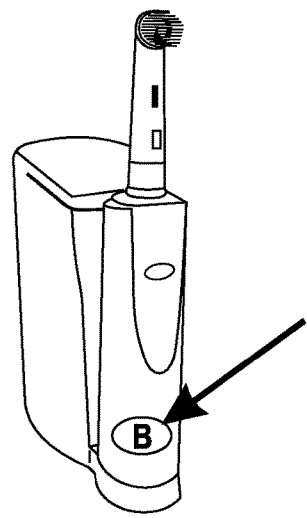
FIG. 1A depicts an exemplary button on a blockchain-enabled electric toothbrush, according to an embodiment of the disclosure.

Exemplary embodiments of the disclosure as described herein generally provide systems and methods for using blockchain technology to securely track and maintain a record of a person's dental history. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Exemplary embodiments of the disclosure provide a method and system includes a digital record of a patient's mouth and dental information, tracks mouth/dental transactions or events, such as using a sensor-enables e-toothbrush, taking x-ray information, using teeth cleaning instruments/devices at a dentalcare center, using dental record process machines, etc., preprocesses dental related inputs using one or more analytics algorithms, and a blockchain system to securely, record, track and maintain a record of mouth/tooth events. Embodiments of the disclosure can instrument and sense dental events using one or more sensors, GUI, existing applications, instead of manually generated dental events and manually managed personal records. Further embodiments focus a block on an organ, such as the mouth or teeth, with possible impact on fraud and forensics, rather than on traditional personal medical health records.

Embodiments of the disclosure can store a record of a patient's tooth treatments/characteristics in the growing block. The block is anchored to a patient and securely tracks the patient through time. Embodiments use blockchain technology to securely track and maintain a record of a patient's mouth/tooth history and events. A patient's tooth transactions are compiled into a chain of mouth/tooth transaction blocks. The chain can be considered a chronicle of the patient's dental/tooth path through time. When a transaction occurs, one or more corresponding dental/tooth parameters, such as treatment, cavity detection, adjacent gum disease, cleaning information, filling material used, x-ray information, etc., are sent to one or more validation modules. The modules establish a validity of the transaction and generate a new block. Once the new block has been calculated, it is appended to the patient's tooth/mouth historic blockchain.

According to embodiments, a transaction that is added to the block can be any tooth/gum item/event. Such items and events include:

cavities, adjacent gum disease, cleaning information;
filling material used, x-ray information, fluoride treatments;
tooth anomalies/stains/wear, missing teeth, observations regarding color and discoloration;
observations on the presence of dental implants and crowns, root canals, etc.;
diet of person, pain level on a pain index; and
the patient's tooth brushing activities, etc.

One or more of these can be securely stored in a growing block. Blockchains according to embodiments may also include chronicle of a patient's dental related events through the life of a dental record, or for a period of time T, where the dental related events further include:
one or more interactions with dental technology, such as an e-toothbrush, filling tools, etc.;
one or more interactions with a dental care professional or automated dental systems, such as an x-ray system that adds to the block when it takes a photo and exposes a person to x-rays;
pulpotomy, pulpectomy, apicoectomy, veneers, bridges, implant-supported prosthesis, fiberotomy, etc.;
gum disease, trauma or injury, dry sockets, impacted teeth, malocclusion;
toothwear, sinusitis, neuralgia, cracked tooth;
sensitivity to heat, cold, sweets;
abrasion, erosion, attrition, bruxism, fracture;
tooth decay (cavities), fractured teeth, worn fillings, worn tooth enamel, exposed tooth root;
fillings with gold, porcelain, silver amalgam (mercury mixed with silver, tin, zinc, or copper), or tooth-colored, plastic, and composite resin fillings.

A GUI can be used to control what and when information is stored in the block, or what kinds of additions to the block can be automated. For example, a dentist or dental assistant may click on a computer screen showing a map of a person's mouth.

Content can be added to the block when a patient goes to a dentists and some observation or action is taken, such as x-rays, teeth cleaning, teeth probing, teeth/gum observations, treatments, etc. Information is appended based on interactions of dentalcare professional or an automated system, such as an x-ray system that automatically adds to the block when it takes a photo and exposes a person to x-rays.

A transaction related to person's tooth record can be further based the a person's teeth brushing activities, such as using an electronic toothbrush, in which a record of the activity can be added to the block in real-time, as the person cleans/brushes/washes his/her teeth. An electronic toothbrush according to an embodiment has a GUI or control to indicate to the user what and when information is stored in the block.

The rate of addition of information to the blockchain can be automatically changed by a risk assessment or forecast. For example, the rate may change in a setting where a risk is forecast to increase. This may depend on the risk level or importance of a tooth being treated, a risk of infection, a risk of cosmetic problems, a risk of pain or abscess, etc.

The content may be a scalar or a vector quantity. For example, one or more risk characteristics or risk based needs may have more than one dimension. Some exemplary risk dimensions include: risk of structural damage and breakup of a tooth, risk of bacterial infection, risk of a cosmetically poor outcome, risk of discomfort during a procedure and also after the procedure due to imperfect tooth interfaces.

The type or nature of the added content can be changed by context, such as a reason or complaint that triggers a visit to a dentist, a person's age, a person's overall health, the number of real teeth that remain in mouth, tooth crowding, a patient's diet. For example, if a person has a history of periodontal disease, slightly higher resolution x-rays should be stored to the block, whereas if there is no history, then low-resolution, such as down-sampled, images may be stored, partly for reasons of network speed and storage constraints.

Content can be added to the block in real-time, as a dentalcare professional inspects or treats a mouth or tooth.

In one embodiment, a risk assessment or forecast is based on an electronic toothbrush, with advanced visual analytics and deep neural nets to aid identification with confidence levels to scan the tooth and detect formation of tartar/plaque, accumulation of bacteria, formation of cavities, etc., such as by observing colors changes from yellow to black and by obtaining the historical tooth's block identifier. An electronic toothbrush according to an embodiment can also include one or more smell sensors to detect the smell or odor of the mouth. This approach need not disintermediate the dentalcare professional, but can help guide a user to seek attention. A system according to an embodiment can learn and improve its algorithms through time.

A system according to an embodiment is privacy preserving and, to some extent places privacy in the hands of a patient and gives access to a patient. A dentist or dental group that offers this feature would be more appealing than one that does not.

According to an embodiment, a system and method for creating and determining a treatment or procedure for an individual or a cohort uses chaincodes to validate transactions. These chaincodes implement one ore more business or medical logics for tracking and validating unsafe treatments by obtaining historical tooth's block identifier.

According to an embodiment, validating tooth transactions includes a set of tooth tokens representative of a person's dental health or features of a mouth or tooth. The tooth tokens include inputs such as user generated queries, treatment results or probe findings, responses to user queries, etc., user cohort and context, and outputs such as risk assessment, tooth forecasts, etc.

A validation device according to an embodiment can:
obtain a historical block identifier from a tooth historical blockchain representative of historical activities the user conducted with respect to the tooth.
receive one or more validity requirements with respect to a user's activities related to the tooth,
obtain a validation token indicative of a validity of a user's actions based on the set of tooth tokens comprising one or more inputs; and
execute the chaincode block for a transaction against the validation requirement as a function of the following tooth parameters: the validation token, historical tooth's block identifier, and the set of tooth tokens.

According to an embodiment, the rate of transaction validation and the rate of adding to the block is determined based on context analysis of user and tooth data, the criticality of the tooth features or concerns, the capacity of the person, i.e., can he/she brush teeth every day or after meals, etc.

Embodiments of the disclosure can provide a method and system for detecting or predicting a concern with respect to a tooth, observation, or treatment breach based on the user's tooth history, cohort, and context, by obtaining the historical tooth's block identifier, where the detection or prediction of a concern can be based on advanced real-time vulnerability scanning and detection algorithms that include learning based methods. Embodiments of the disclosure can further may track and store tool history per tooth, related to which tools were used during a treatment.

Embodiments of the disclosure can provide a specialized risk assessment chaincode to validate a transaction related to a sensitivity that may be caused by a small amount of decay, a loose filling or by minimal gum recession that exposes small areas of the root surface. This chaincode generates an event to compute a sensitivity score, such as sensitivity to hot and cold foods. A sensitivity score can be used by one or more customized modules to generate a list of actions for the patient. Examples of such actions include using toothpastes made for sensitive teeth, brushing up and down with a soft brush, since brushing sideways wears away exposed root surfaces, etc.

Figure 1B:
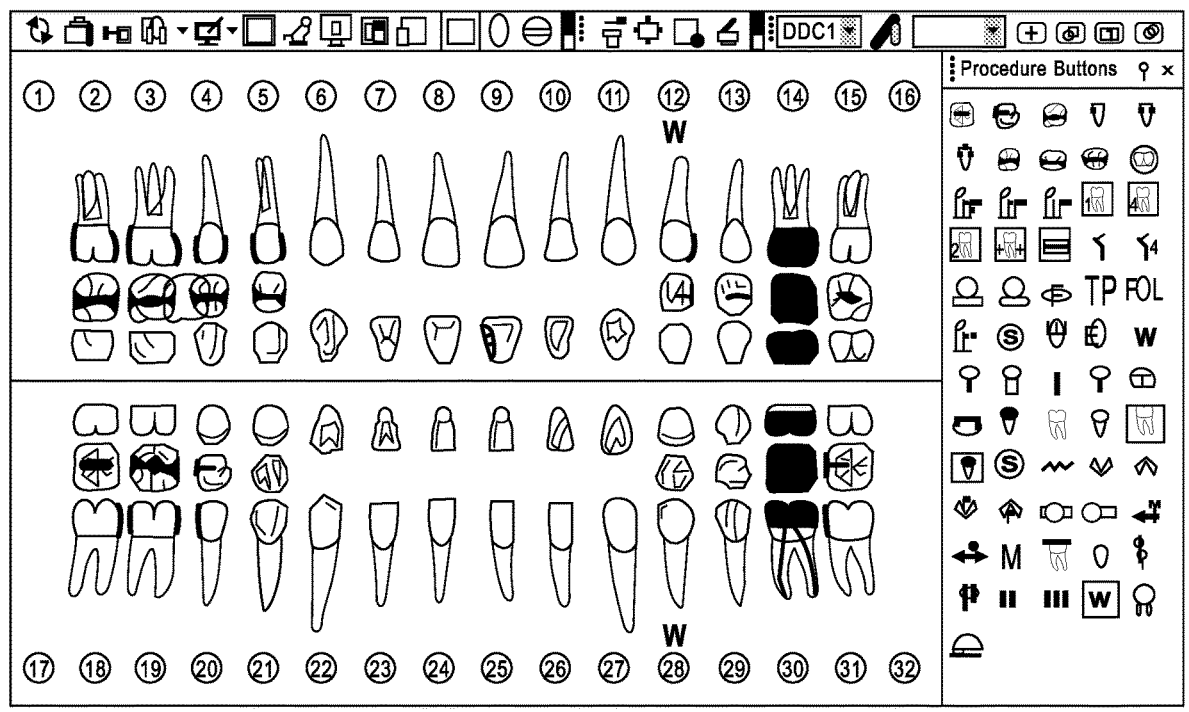
FIG. 1B illustrates an exemplary electronic dental record, according to an embodiment of the disclosure.

Embodiments of the disclosure can provide a button for a user to add to the chain, if desired, FIG. 1A depicts an exemplary B button on a blockchain-enabled electric toothbrush. FIG. 1B illustrates an exemplary electronic dental record, with teeth shown on the left and various procedure buttons on the right. When a button is selected, a blockchain block may be updated. FIG. 1C illustrates dental transaction records added to a blockchain block. The records include a date, an event code, a tooth and surface code, and a description of the transaction. FIG. 1D illustrates additional exemplary, non-limiting buttons for adding blocks to the blockchain, where the buttons are labeled for various dental items and events, such as crowns, inlays, veneer, implants, temperature test, decay, watching teeth, etc. FIG. 1E depicts a tooth numbering system, to help provide digital information for the block.

In some cases, a blockchain based system and method according to embodiments recommends updating a dental system or treatment based on the risk assessment or risk prediction based on obtaining historic events of the patient interaction with the dentist.

A risk assessment or forecasting according to an embodiment can further trigger actions, such as recommending visiting a dentist, brushing more frequently, using a water flossing device, etc., if a risk level is greater than a threshold. For example, based on the validity of a transaction related to the detection of a cavity formation, a system according to an embodiment notifies the person to visit a dentist within a certain time window. A system according to an embodiment can be integrated with an existing dental system and can automatically schedule an appointment based on predicted risk level.

A system according to an embodiment can be used by a dentist or dental hygienist of the patient.

Figure 2A:
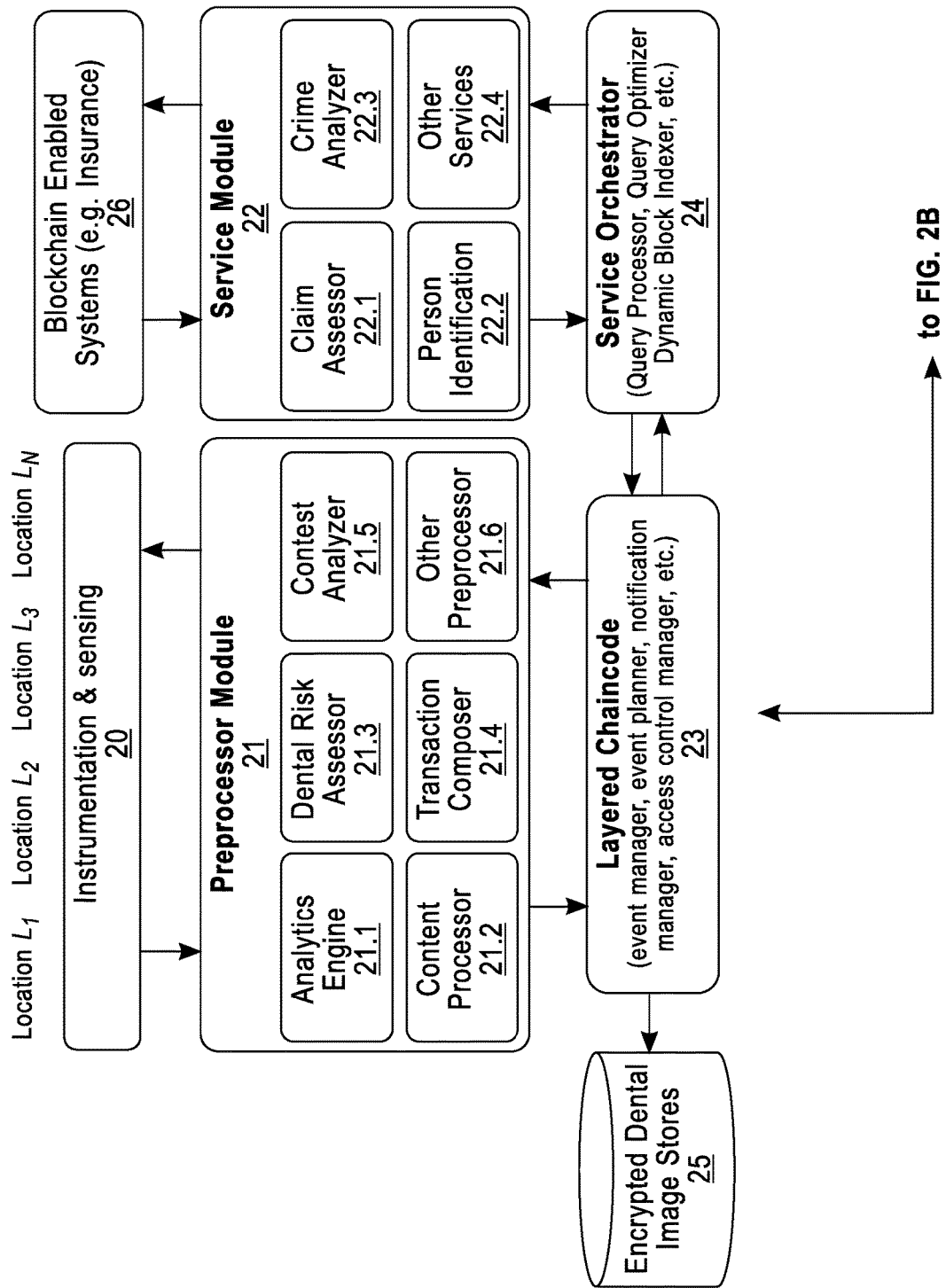
FIG. 2A illustrates an exemplary system architecture, according to an embodiment of the disclosure.

FIG. 2A illustrates an exemplary system architecture according to an embodiment. Referring to the figure, a system according to an embodiment includes an instrumentation and sensing module 20, a preprocessor module 21, a service module 22, a blockchain network of layered chaincode 23, and a service orchestrator 24.

The instrumentation and sensing module 20 includes a plurality of instruments and sensors at various locations that monitor and collect various events and data from a plurality of data sources, such as user or system generated data such as physical reports, examination results, etc. The sensors and instruments include electronic toothbrush sensors, visual analytics, dental instruments, etc. For example, one or more smell sensors may detect the smell or odor of the mouth, and module summarizes and sends the event data to the preprocessor module for analytics, such as cloud-based or on end-user based on a mobile device.

The preprocessor module 21 receives the data from instrumentation and sensing layer and applies various modules, such as an analytics engine 21.1, a risk assessor 21.3, and a context analyzer 21.5 that uses, e.g., machine learning and deep neural nets, to analyze the event streams, characterize the dental condition and context, and determine the risk to a patient's teeth. The risk assessor further uses, e.g., deep neural nets, to identify a confidence level of the risk, accumulation of bacteria, formation of cavities, etc., by, e.g., observing colors changes from yellow to black and also obtaining the tooth's historical block identifier. A content analyzer 21.2 analyzes documents, such as x-ray documents, complaint documents that trigger dental visits, a person's age, a person's overall health, the number of remaining real teeth in a mouth, tooth crowding, a patient's diet. For example, if a person has a history of periodontal disease, perhaps slightly higher resolution x-rays may be stored to the block, whereas if there is no history, then lower-resolution, such as down-sampled, images can be stored, for reasons of network speed and storage constraints. A transaction composer 21.4 uses the event streams and analysis results and prepares and packages a payload to be appended to the blockchain and sends the payload to the blockchain network 23. The blockchain network 23 uses layered chaincodes, such as event managers, event planners, notification managers, access control managers, etc. to manage the network. The blockchain network 23 is connected to an encrypted dental image store 25, which is a database for storing dental records and chaincodes of the blockchain network 23. The blockchain network is described in detail with respect to FIG. 2B.

The service module includes a claim assessor 22.1, a crime analyzer 22.3, a person identifier 22.2, and other services 22.4 that perform advanced services based on data from various blockchain enabled systems 26, such as insurance providers, banks, dentalcare providers, and that include claim assessment, crime analysis, etc., from events stored on blockchain. An example of a service module is one that triggers actions, such as recommending visiting a dentist, brushing more frequently, using a water flossing device, etc., if a risk level is greater than a threshold based on a risk assessment. Based on the validity of a transaction event related to the detection of a cavity formation, the service module generates a notification for a person to visit a dentist within a time window T. A system according to an embodiment can be integrated with an existing dental system and can automatically schedule an appointment based on a predicted risk level.

Figure 2B:
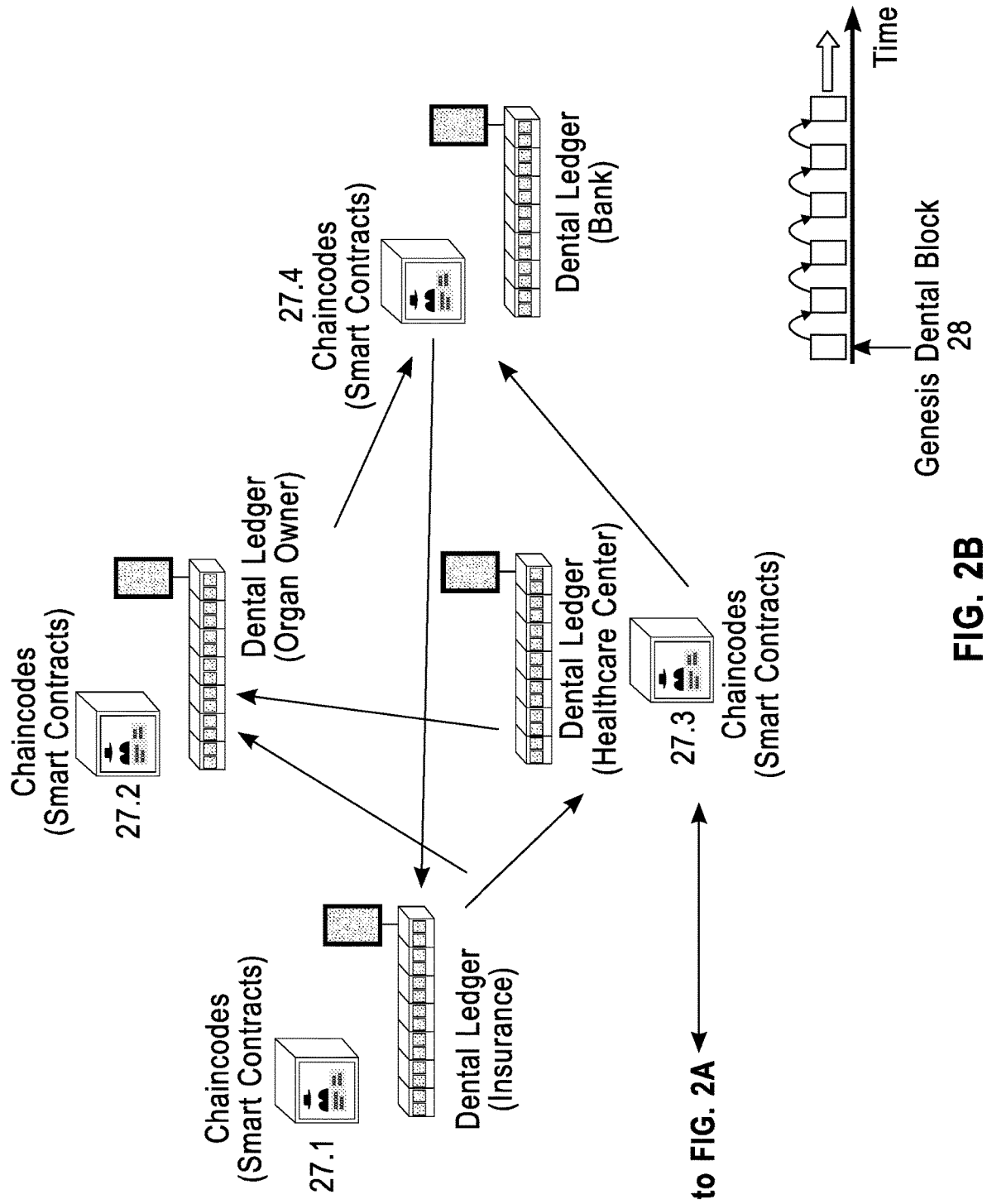
FIG. 2B depicts an exemplary blockchain network setup, according to an embodiment of the disclosure.

FIG. 2B depicts an exemplary blockchain network setup according to an embodiment. A blockchain network is a collection of smart contracts that can manage dental events. Referring now to the figure, a blockchain network according to embodiments includes a plurality of nodes 27.1, 27.2, 27.3, 27.4, for, respectively, insurance, an organ owner, a bank, and a dentalcare center. Each node includes chaincodes and an associated dental ledger. Item 28 depicts a genesis dental block of a ledger, which is the very first block in a ledger chain. The ledger chain is a linked list, with each block pointing to its successor. Examples of chaincodes include risk assessment chaincode, an access control (ACL) chaincode that controls privileges and access rights of a dental record, claim validator chaincode, event chaincode, and record manager. These chaincodes are deployed at each node of the blockchain network for managing school systems. According to embodiments, all the functionalities and services are governed by the necessary smart contracts; such as process chaincode ensures the corresponding processes are followed and agreed up on by all the nodes, etc. Each dental ledger block includes transaction records related to one or more of cavities, adjacent gum disease, cleaning information, filling material, X-ray information, fluoride treatments, tooth anomalies/stains/wear, missing teeth, observations regarding color and discoloration, observations regarding dental implants, crowns, root canals, etc., brushing activities, etc.

Figure 3:
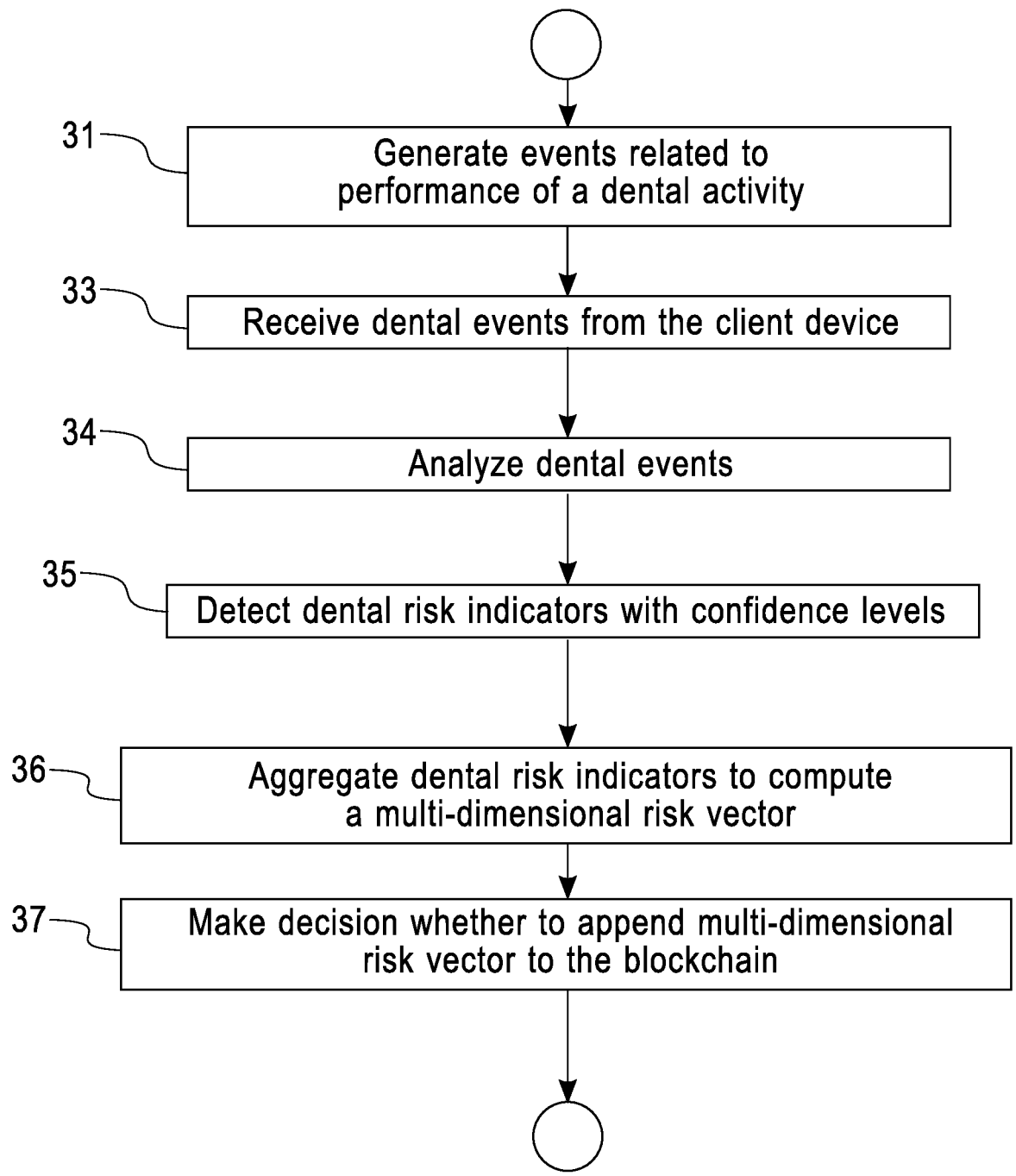
FIG. 3 is a flow chart of a method for generating an event or transaction for inclusion in a blockchain, according to an embodiment of the disclosure.

FIG. 3 is a flow chart of a method for generating an event or transaction for inclusion in a blockchain, according to an embodiment of the disclosure. A method begins at step 31 when a client device performs a dental related activity or event at a given location. The client device can be an e-toothbrush with one or more sensors, an X-ray machine, tooth cleaning instruments/devices at a dentalcare center, a dental record processing machine, etc. The dental related event or activity can include registering teeth for the first time, brushing/cleaning teeth, filling a cavity, visiting a dentist where some observation or action is taken, such as x-rays, teeth cleaning, teeth probing, teeth/gum observations, treatments, etc. The client device generates one or more input signals related to the dental activity being performed at the location. At step 33, the preprocessor system 21 of FIG. 2A receives the one or more signals from the client device in one or more input forms, such as an image scan, smell sensor data, x-ray information, location, etc. The preprocessor system 21 analyzes the dental input events using real-time visual analytics, neural networks, etc. at step 34. At step 35, the preprocessor system 21, detects various dental feature and risk indictors, such as tartar/plaque formation, bacteria accumulation, cavity formation, mouth odor, etc., using machine learning techniques such as deep neural networks to aid identification with associated confidence levels. At step 36, the preprocessor system 21 aggregates the various dental feature and risk indictors to compute a multi-dimensional feature vector, and at step 37, makes a decision for appending the multi-dimensional feature vector to the blockchain. The appending decision can be based in part on a rate at which such information should be added to the blockchain.

Figure 4:
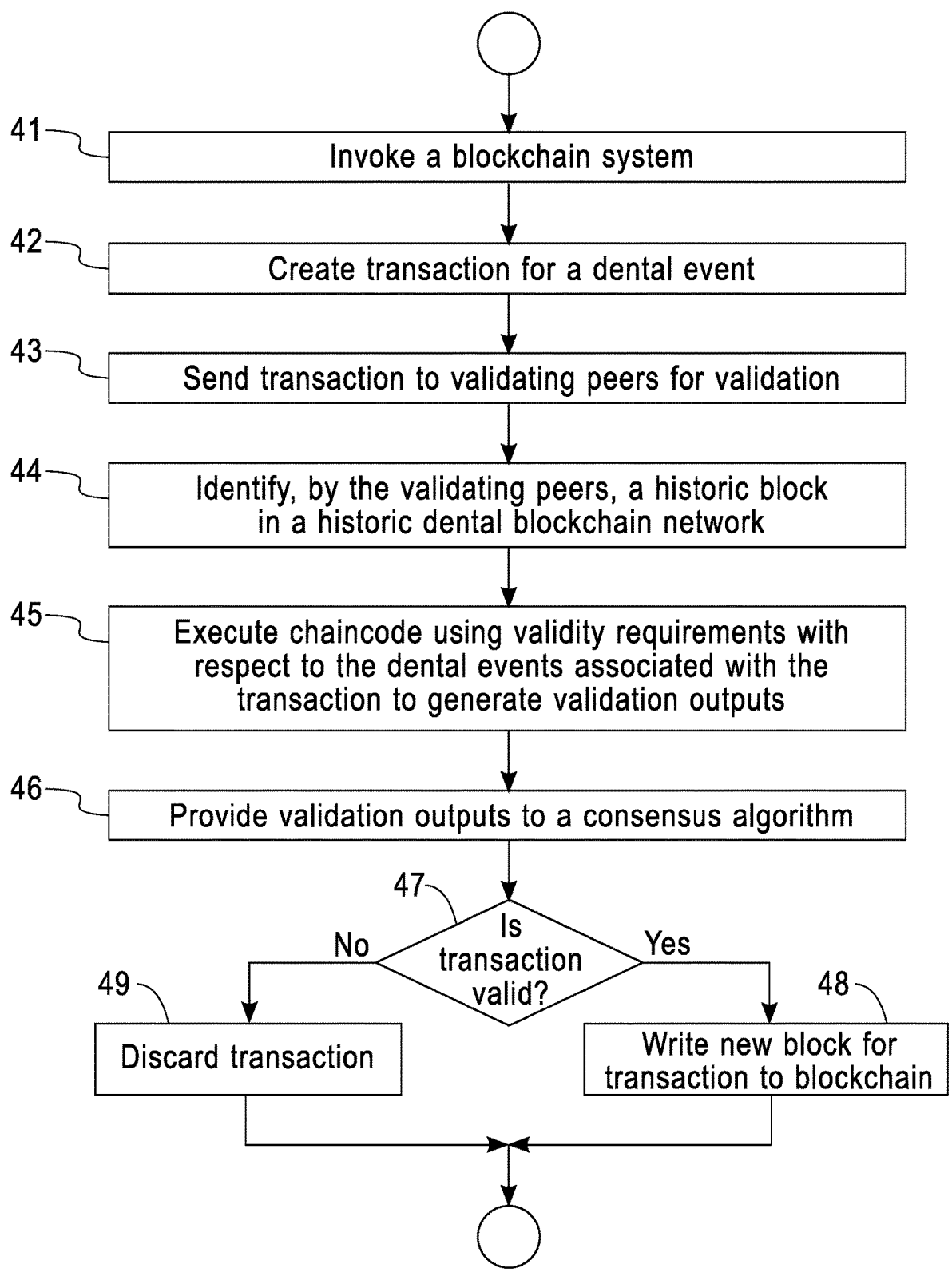
FIG. 4 is a flowchart of a method for validating a transaction, according to an embodiment of the disclosure.

FIG. 4 is a flowchart of a method for validating a transaction, to determine whether to append information to the blockchain, according to an embodiment of the disclosure. A method begins at step 41 by invoking a blockchain system by the preprocessor 21 of FIG. 2A. A transaction for a dental event, such as the multi-dimensional feature vector, is created at step 42, and the transaction is sent to validating peers for validation at step 43. At step 44, a historic block is identified in a historic dental blockchain network by the validating peers, which execute chaincode using validity requirements with respect to the dental events associated with the transaction and generate validation outputs, at step 45. At step 46, the validation outputs are received by a consensus algorithm, which determines at step 47 whether a consensus regarding validation has been reached. If the transaction has been validated, a new block for that transaction is written to the blockchain at step 48, otherwise, at step 49, the transaction is discarded.

A blockchain-implemented system according to an embodiment can be used to facilitate lock-in attribution, secure sharing, improvement visibility, and provide certificates of authenticity. For lock in attribution, a system according to an embodiment can create a permanent and unbreakable link between the user and his/her tooth information. That link, the record of mouth and tooth information, can be forever verified and tracked. For secure sharing, a system according to an embodiment can securely share one's tooth and mouth information with others. Transferring tooth information can be as easy as transferring or copying a mouth information record. Other embodiments can trace when and how a patient's dental health improves. A system according to embodiments can show how the contents or events of a person's dental health have appeared and changed over time. Further embodiments can a certificate of authenticity (COA) for each logged event, a built in unique cryptographic ID with a complete ownership history. A COA can be verified anytime and printed out and used by crime investigators, insurance companies, etc.

Further embodiments of the disclosure can provide a higher-level interface to make a blockchain dental system easier to use by a patient, dentists or medical processional. For example, consider that a dentist or dental professional can enter a patient dental record into the database via a global computer network and designate other users who ma access the record. After an initial authorization, a patient user can be directed to the home page of the dentist who provided the patient authorization code to the patient user. From this dentist's home page, the patient user can enter any of several different sections, such as a patient general chart, pharmacy information, search, help, and dental treatment transaction information. Once the patient enters a patient general chart section, the patient user may access various areas relating to his or her dental records, such as medical/dental history, general exams, and dental treatment charts.

Further embodiments of the disclosure can provide a higher-level interface to enable searches of dental records based on similarities in information contained in a blockchain system according to an embodiment. An automated identification system according to an embodiment can include a search and retrieval stage based on potential similarities and a verification stage to match based upon the comparisons of dental images. For example, an automated dental identification system can enhance raw subject dental records and extract high level features. When dental records are searched, a candidate list can be created. A system according to an embodiment can compare a subject dental record to the candidate list to categorize potential matches, and inspect potential matches for a final determination.

In further embodiments for forensic applications, the mouth/tooth block can contain information on DNA, the dentin pulp complex, and if applicable, a determination of possible causes of death.

Blockchains:

A blockchain is a distributed network. A blockchain can be understood as the evolution of the ledger, a record-keeping tool that's been central to commerce since ancient times. Ledgers track the movement of assets, whether they're parcels of land or shares in a company. In the age of the cloud, it's possible for a network of banks or companies in a supply chain to maintain what's called a distributed ledger that all authorized participants can tap into without needing to go through an intermediary.

Although embodiments of the disclosure do not use the blockchain for currency, in the context of the first digital currency, bitcoin, a blockchain is a digital ledger that records every bitcoin transaction that has ever occurred. It is protected by cryptography so powerful that breaking it is considered to be impossible. Furthermore, the blockchain resides not in a single server, but across a distributed network of computers. Thus, when a new transaction occurs, the blockchain is authenticated across this distributed network, after which the transaction is included as a new block on the chain.

A blockchain implementation usually includes two kinds of records: transactions and blocks. Transactions are the content that is stored in the blockchain. Transactions are created by participants using the blockchain system. In the case of a cryptocurrency, a transaction is created any time a cryptocurrency owner sends cryptocurrency to someone. System users create transactions that are passed from node to node on a best-effort basis. The system implementing the blockchain defines a valid transaction. In cryptocurrency applications, a valid transaction must be digitally signed, spend one or more unspent outputs of previous transactions, and the sum of the transaction outputs must not exceed the sum of the inputs.

Blocks record and confirm when and in what sequence transactions enter and are logged in the blockchain. Blocks are created by users known as miners who use specialized software specifically designed to create blocks. In a cryptocurrency system, miners are incentivized create blocks to collect two types of rewards: a pre-defined per-block award, and a fee offered within the transaction itself, payable to any miner who successfully confirms the transaction.

Every node in a decentralized system has a copy of the block chain. This avoids the need to have a centralized database managed by a trusted third party. Transactions are broadcast to the network using software applications. Network nodes can validate transactions, add them to their copy and then broadcast these additions to other nodes. To avoid the need for a trusted third party to timestamp transactions, decentralized blockchains use various timestamping schemes, such as proof-of-work.

Figure 5:
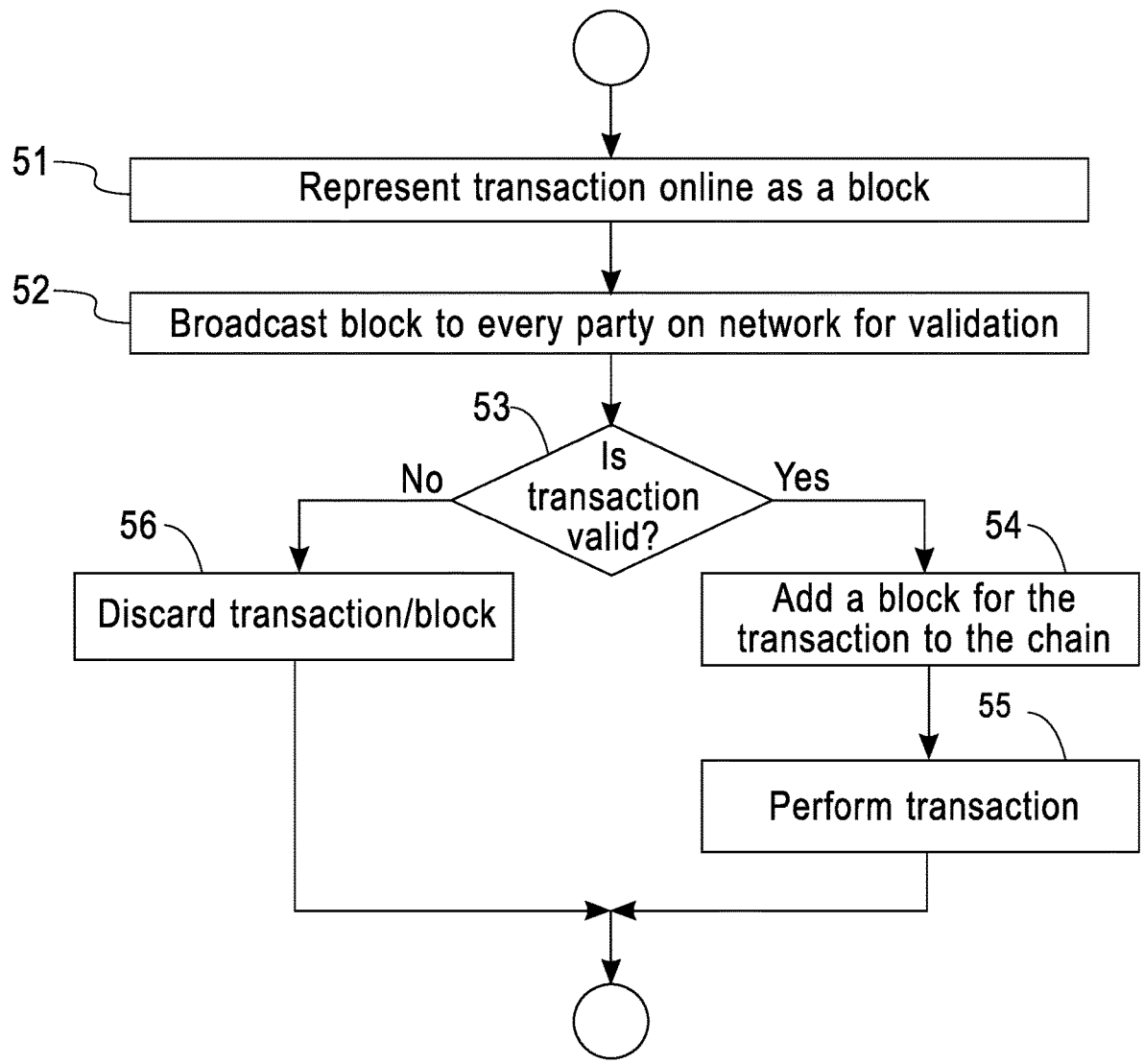
FIG. 5 is a flowchart of how a blockchain works, according to an embodiment of the disclosure.

An exemplary blockchain works as follows, with reference to FIG. 5. Suppose A wants to send money to B. At step 51, the "send money from A to B" transaction is represented online as a block. This block is then broadcast to every party on the network at step 52. The parties in the network need to approve the transaction as valid. Once the transaction has been approved, at step 53, the block can be added to the chain at step 54, which provides an indelible and transparent record of the transaction. At step 55, the transaction can be performed, i.e., the money can then be transferred from A to B. If the transaction is not approved, the block and the transaction are discarded at step 56. Unlike a centralized ledger that tracks asset movements within the financial system between entities, a distributed ledger eliminates the need for a central authority to certify asset ownership. Instead, asset ownership is held and verified by many entities, thus reducing fraud and manipulation.

Blockchains have the following properties. A blockchain enables independent nodes to converge on a consensus of the latest version of a large data set such as a ledger, even when the nodes are run anonymously, have poor interconnectivity and have operators who are dishonest or malicious. A blockchain enables any well-connected node to determine, with reasonable certainty, whether a transaction does or does not exist in the data set. A blockchain enables any node that creates a transaction to, after a confirmation period, determine with a reasonable level of certainty whether the transaction is valid, able to take place and become final, i.e., that no conflicting transactions were confirmed into the block chain elsewhere that would invalidate the transaction, such as the same currency units, double-spent somewhere else. A blockchain imposes a prohibitively high cost to attempts to rewrite or alter transaction history. A blockchain provides an automated conflict resolution that ensures that conflicting transactions, such as two or more attempts to spend the same balance in different places, never become part of the confirmed data set. A blockchain-based system is more secure, in that criminals cannot commandeer individual machines to gain access to a network.

A blockchain according to an embodiment of the disclosure provides the infrastructure and fabric services for securely and transparently storing, tracking and managing transactions on records. The blockchain contains a verifiable record of every single transaction ever made within the system. Once data are entered onto the blockchain, it can never be erased (immutability) or changed without introducing a new blockchain entry, thus ensuring auditability and verifiability of data.

A blockchain according to an embodiment of the disclosure is based on a distributed database of records of all transactions or digital events that have been executed and shared among participating parties. An individual transaction in the blockchain is validated or verified through a consensus mechanism incorporating a majority of the participants in the system. This allows the participating entities to know for certain that a digital event happened by creating an irrefutable record in a permissioned public ledger.

As disclosed above, transactions associated with any dental entity is compiled into a chain of "transaction blocks" that constitutes the lifelong record of what has happened to that entity. The chain can be considered a chronicle of a dental entity's path through time. When a transaction is executed, its corresponding chaincode is executed by several validating peers of the system. The peers establish the validity of the transaction parameters and once they reach consensus, a new block is generated and appended onto the blockchain network.

A blockchain according to an embodiment of the disclosure is a distributed ledger that persists and manages digital events, called transactions, shared among several participants, each having a stake in these events. The ledger can only be updated by consensus among the participants. Furthermore, once transactions are recorded, they can never be altered. They are immutable. Every such recorded transaction is cryptographically verifiable with proof of agreement from the participants, thus provided a robust provenance mechanism tracking their origination.

Typical solutions built on a blockchain according to an embodiment of the disclosure can be broken down into several components: membership service, validating peers, non-validating peers, and one or more client applications. All of these components jointly make up a blockchain application. There can be multiple blockchains, each one having its own operating parameters and security requirements. Membership services manage data access. Validating peers are designated nodes that participate in consensus algorithms and can validate the data that gets persisted on the blockchain and execute chaincode against the data contained in the ledger. Non-validating peers maintain request services from membership services and validating peers on behalf of external client applications.

System Implementations

It is to be understood that embodiments of the present disclosure can be implemented in various forms of hardware, software, firmware, special purpose processes, or a combination thereof. In one embodiment, an embodiment of the present disclosure can be implemented in software as an application program tangible embodied on a computer readable program storage device. The application program can be uploaded to, and executed by, a machine comprising any suitable architecture. Furthermore, it is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed. An automatic troubleshooting system according to an embodiment of the disclosure is also suitable for a cloud implementation.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least live characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for loadbalancing between clouds).

A cloud computing environment is service oriented with a focus on statelessness, low coupling, modularity, and semantic interoperability. At the heart of cloud computing is an infrastructure comprising a network of interconnected nodes.

Figure 6:
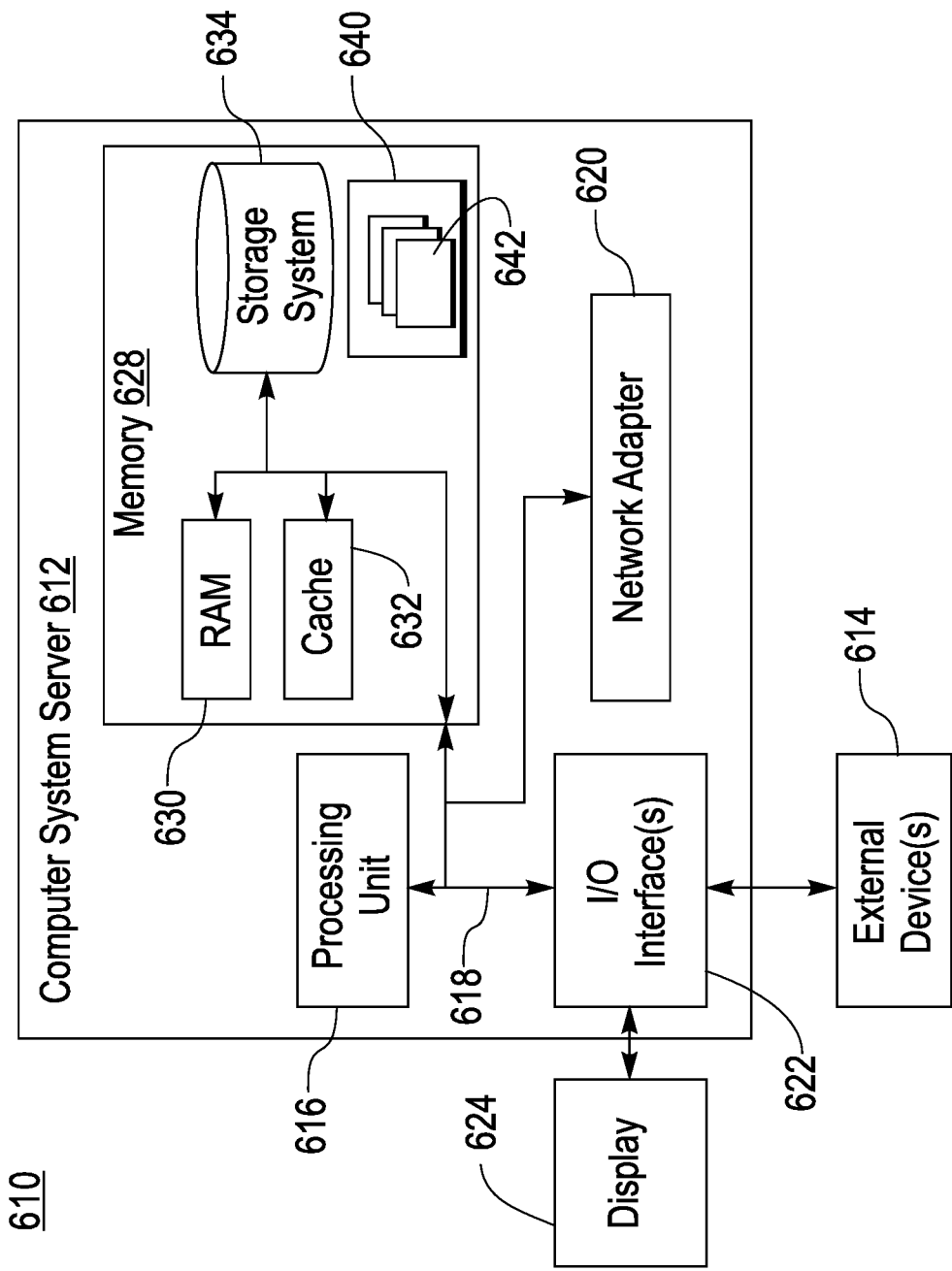
FIG. 6 is a schematic diagram of an example of a cloud computing node, according to an embodiment of the disclosure.

Referring now to FIG. 6, a schematic of an example of a cloud computing node is shown. Cloud computing node 610 is only one example of a suitable cloud computing node and is not intended to suggest any limitation as to the scope of use or functionality of embodiments of the disclosure described herein. Regardless, cloud computing node 610 is capable of being implemented and/or performing any of the functionality set forth hereinabove.

In cloud computing node 610 there is a computer system/server 612, which is operational with numerous other general purpose or special purpose computing system environments or configurations. Examples of well-known computing systems, environments, and/or configurations that may be suitable for use with computer system/server 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 612 may be described in the general context of computer system executable instructions, such as program modules, being executed by a computer system. Generally, program modules may include routines, programs, objects, components, logic, data structures, and so on that perform particular tasks or implement particular abstract data types. Computer system/server 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 612 in cloud computing node 610 is shown in the form of a general-purpose computing device. The components of computer system/server 612 may include, but are not limited to, one or more processors or processing units 616, a system memory 628, and a bus 618 that couples various system components including system memory 628 to processor 616.

Bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 612 typically includes a variety of computer system readable media. Such media may be any available media that is accessible by computer system/server 612, and it includes both volatile and non-volatile media, removable and non-removable media.

System memory 628 can include computer system readable media in the form of volatile memory, such as random access memory (RAM) 630 and/or cache memory 632. Computer system/server 612 may further include other removable/non-removable, volatile/non-volatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 618 by one or more data media interfaces. As will be further depicted and described below, memory 628 may include at least one program product having a set (e.g., at least one) of program modules that are configured to carry out the functions of embodiments of the disclosure.

Program/utility 640, having a set (at least one) of program modules 642, may be stored in memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the disclosure as described herein.

Computer system/server 612 may also communicate with one or more external devices 614 such as a keyboard, a pointing device, a display 624, etc.; one or more devices that enable a user to interact with computer system/server 612; and/or any devices (e.g., network card, modem, etc.) that enable computer system/server 612 to communicate with one or more other computing devices. Such communication can occur via Input/Output (I/O) interfaces 622. Still yet, computer system/server 612 can communicate with one or more networks such as a local area network (LAN), a general wide area network (WAN), and/or a public network (e.g., the Internet) via network adapter 620. As depicted, network adapter 620 communicates with the other components of computer system/server 612 via bus 618. It should be understood that although not shown, other hardware and/or software components could be used in conjunction with computer system/server 612. Examples, include, but are not limited to: microcode, device drivers, redundant processing units, external disk drive arrays, RAID systems, tape drives, and data archival storage systems, etc.

Figure 7:
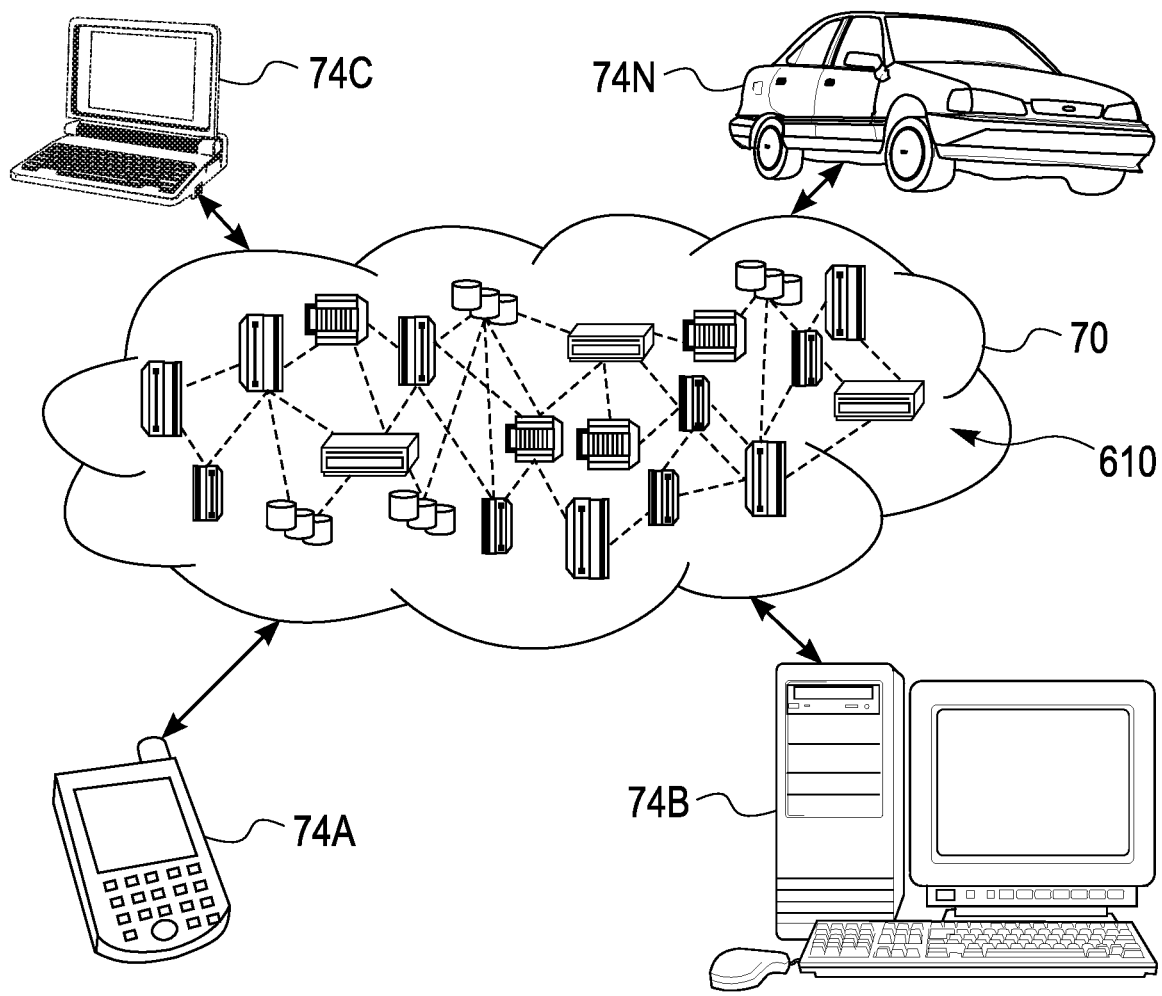
FIG. 7 illustrates an exemplary cloud computing environment, according to an embodiment of the disclosure.

Referring now to FIG. 7, an illustrative cloud computing environment 70 is depicted. As shown, cloud computing environment u0 comprises one or more cloud computing nodes 610 with which local computing devices used by cloud consumers, such as, for example, personal digital assistant (PDA) or cellular telephone 74A, desktop computer 74B, laptop computer 74C, and/or automobile computer system 74N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 70 to offer infrastructure, platforms and/or software as services for which a cloud consumer does not need to maintain resources on a local computing device. It is understood that the types of computing devices 74A-N shown in FIG. 7 are intended to be illustrative only and that computing nodes 610 and cloud computing environment 70 can communicate with any type of computerized device over any type of network and/or network addressable connection (e.g., using a web browser).

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A method of managing dental records using a blockchain, comprising the steps of:
   receiving, from a dental device, one or more signals associated with a dental activity being performed by the dental device;
   detecting dental feature indictors with associated confidence levels by analyzing the dental signals;
   aggregating the dental feature indictors to compute a multi-dimensional feature vector;
   creating a transaction for the multi-dimensional feature vector;
   sending the transaction to validating peers on the blockchain network for validation;
   receiving validation outputs by a consensus algorithm, wherein the validation outputs are generated by chaincodes executed by the validation peers using validity requirements with respect to the dental events associated with the transaction; and
   writing a new block for the transaction to the blockchain, when the consensus algorithm validates die transaction.

2. The method of claim 1, wherein the blockchain includes a record of a patient's dental related features and events through the life of the patient, or for a predetermined period of time, wherein the dental related features and events include information on one or more of cavities, gum disease, dry sockets, impacted teeth, malocclusion, toothwear, sinusitis, neuralgia, cracked teeth, fractured teeth, abrasion, missing teeth, erosion, attrition, bruxism fracture, worn fillings, worn tooth enamel, and exposed roots; sensitivity to heat, cold, and sweets; filling materials, X-rays treatments, fluoride treatments, pulpotomies, pulpectomies, apicoectomies, veneers, bridges, implants, fiberotomies, implants, crowns, root canals; observations regarding color and discoloration; diet and pain level; interactions with dental technology; and interactions with a dental care professionals or automated dental systems.

3. The method of claim 1, wherein the dental device includes a home signal-enabled toothbrush, a dental office tooth cleaner, a signal-enabled dental office tooth probe, an X-ray machine, a dental office camera, and the one or more events associated with a dental activity include X-ray treatments, teeth cleaning, teeth probing, and teeth and gum observations.

4. The method of claim 1, further comprising automatically changing a rate of generating transactions related to a dental record based on a risk assessment or forecast.

5. The method of claim 1, further comprising changing a type of in added written to the blockchain based on a context of a patient.

6. A non-transitory program storage device readable by a computer, tangibly embodying a program of instructions executed by the computer to perform the method steps for managing dental records using a blockchain, comprising the steps of:
   receiving, from a dental device, one or more signals associated with a dental activity being performed by the dental device;
   detecting dental feature indictors with associated confidence levels by analyzing the dental signals;
   aggregating the dental feature indictors to compute a multi-dimensional feature vector;
   creating a transaction for the multi-dimensional feature vector;
   sending the transaction to validating peers on the blockchain network for validation;
   receiving validation outputs by a consensus algorithm, wherein the validation outputs are generated by chaincodes executed by the validation peers using validity requirements with respect to the dental events associated with the transaction; and
   writing a new block for the transaction to the blockchain, when the consensus algorithm validates the transaction.

7. The computer readable program storage device of claim 6, wherein the blockchain includes a record of a patient's dental related features and events through the life of the patient, or for a predetermined period of time, wherein the dental related features and events include information on one or more of cavities, gum disease, dry sockets, impacted teeth, malocclusion, toothwear, sinusitis, neuralgia, cracked teeth, fractured teeth, abrasion, missing teeth, erosion, attrition, bruxism, fracture, worn fillings, worn tooth enamel, and exposed roots; sensitivity to heat, cold, and sweets; filling materials, X-rays treatments, fluoride treatments, pulpotomies, pulpectomies, apicoectomies, veneers, bridges, implants, fiberotomies, implants, crowns, root canals; observations regarding, color and discoloration; diet and pain level; interactions with dental technology; and interactions with a dental care professionals or automated dental systems.

8. The computer readable program storage device of claim 6, wherein the dental device includes a home signal-enabled toothbrush, a dental office tooth cleaner, a signal-enabled dental office tooth probe, an X-ray machine, a dental office camera, and the one or more events associated with a dental activity include X-ray treatments, teeth cleaning, teeth probing, and teeth and gum observations.

9. The computer readable program storage device of claim 6, wherein the method further comprises automatically changing a rate of generating transactions related to a dental record based on a risk assessment or forecast.

10. The computer readable program storage device of claim 6, wherein the method further comprises changing a type of information added written to the blockchain based on a context of a patient.

* * * * *